(12) United States Patent
Beale et al.

(10) Patent No.: US 6,221,836 B1
(45) Date of Patent: Apr. 24, 2001

(54) COMPOSITION OF PYRUVATE AND ANABOLIC PROTEIN AND METHOD FOR INCREASING FAT LOSS IN A MAMMAL

(75) Inventors: Paxton K. Beale, San Francisco, CA (US); Donald O. Nickey, Plain City, OH (US); Millard F. Williamson, Fairfield, CA (US)

(73) Assignee: Paxton King Beale, San Francisco, CA (US)

( * ) Notice: Subject to any disclaimer, the term of this patent is extended or adjusted under 35 U.S.C. 154(b) by 0 days.

(21) Appl. No.: 09/213,968

(22) Filed: Dec. 17, 1998

Related U.S. Application Data

(63) Continuation-in-part of application No. 08/951,547, filed on Oct. 16, 1997, now Pat. No. 5,889,040, which is a continuation of application No. 08/686,819, filed on Jun. 26, 1996, now Pat. No. 5,716,926.

(51) Int. Cl.$^7$ .......................... A23L 1/305; A61K 38/17; A61K 38/38
(52) U.S. Cl. ................... 514/2; 424/439; 426/69; 426/648; 426/657; 514/21
(58) Field of Search ..................... 424/439, 440, 424/441, 442; 426/69, 648, 656, 657; 514/2, 21, 423, 529, 563, 557

(56) References Cited

U.S. PATENT DOCUMENTS

| | | | |
|---|---|---|---|
| 4,687,782 | * 8/1987 | Brantman | 514/561 |
| 5,236,712 | * 8/1993 | Fregly et al. | 424/439 |
| 5,374,620 | * 12/1994 | Clark et al. | 514/12 |
| 5,716,926 | * 2/1998 | Beale et al. | 514/2 |
| 5,756,469 | * 5/1998 | Beale | 514/23 |
| 5,889,040 | * 3/1999 | Beale et al. | 514/400 |
| 5,919,767 | * 7/1999 | Beale | 514/23 |
| 6,008,252 | * 12/1999 | Beale | 514/563 |
| 6,019,999 | * 2/2000 | Miller et al. | 424/450 |

* cited by examiner

*Primary Examiner*—Jeffrey E. Russel
(74) *Attorney, Agent, or Firm*—Donald O. Nickey; Sean M. Casey

(57) ABSTRACT

The present invention is based in part upon the discovery that the use of pyruvate in enteral formulations, in combination with an anabolic protein composition, produces a synergistic effect in increasing the lean body mass or muscle tissue of a mammal consuming same. The present invention also provides a method for increasing fat loss or decreasing the percent body fat in a mammal through the administration of an anabolic protein composition. The present invention relates generally to a composition for enhancing the protein concentration or muscle mass of a mammal and a method for enhancing the protein concentration or muscle mass in a mammal. More specifically, the present invention relates to a composition which comprises an anabolic protein composition and optionally pyruvate and/or derivatives thereof. The compositions according to the invention can take the form of powders, liquids, pills, capsules, tablets, food additives, candies or confections.

10 Claims, No Drawings

COMPOSITION OF PYRUVATE AND ANABOLIC PROTEIN AND METHOD FOR INCREASING FAT LOSS IN A MAMMAL

RELATED APPLICATIONS

This is a continuation-in-part of U.S. patent application Ser. No. 08/951,547 filed Oct. 16, 1997 now U.S. Pat. No. 5,889,040, which is a continuation of application Ser. No. 08/686,819 filed Jun. 26, 1996 now U.S. Pat. No. 5,716,926.

TECHNICAL FIELD

The parent applications relate generally to a composition for and method of enhancing the protein concentration or muscle mass of a mammal. This application is also directed to pyruvate and anabolic protein compositions, however, the method of use of the composition is directed to fat and weight loss in a mammal and to decreasing the percent body fat in a mammal. More specifically, the present invention relates to a composition which comprises pyruvate and/or derivatives of pyruvate and a novel blend of proteins and/or amino acids that possesses an amino acid profile that is similar to the amino acid profile of human muscle tissue. The method of the present invention comprises administering to a mammal in need of increasing its rate of fat loss or decreasing the percent body fat, a composition comprising pyruvate and a source of amino nitrogen having specific types and levels of amino acids. The method of this invention results in a synergistic increase of fat loss while at the same time lowering the deposition of body fat. The invention is also directed to the anabolic protein compositions themselves and their use to increase the muscle mass of a mammal while decreasing the percent body fat.

BACKGROUND ART

Athletes engage in strenuous training to accomplish the goals of their sport. People desiring to decrease their percent body fat and lose weight also engage in strenuous exercise. This strenuous training essentially amounts to trauma to the body, in that the human body interprets every strenuous work-out as a threat to its survival. It is known that muscle damage, caused by training, releases the catabolic hormone prostaglandin-E2. Training also causes the release of adrenocorticotropin (ACTH), which is a pituitary hormone. The presence of increased levels of ACTH increases the production of the catabolic hormone cortisol. Cortisol is also known as hydrocortisone, which is a glucocorticoid of the adrenal cortex that is a derivative of cortisone. Hydrocortisone is sometimes used in the treatment of rheumatoid arthritis. Thus, cortisol is a naturally occurring anti-inflammatory steroid. This catabolic hormone results in the release of amino acids from muscle tissue and prevents absorption of glucose. Cortisol, as a catabolic stress hormone, cannibalizes muscle tissue. High cortisol levels also result in the breakdown of connective tissue, lowered immunity and reduced muscle RNA synthesis. While cortisol may be a detriment to the athlete, scientists have conjectured that when the human body is stressed or traumatized, it triggers a "fight or flight" survival response. The biological design of cortisol is such that when a human is threatened, cortisol levels rise and mobilize the body for action by breaking down fat and muscle stores for emergency energy. Cortisol also reduces swelling in the event of injury. After the threat or trauma has subsided, cortisol levels return to normal. The cortisol-stress relationship is designed for intermittent physical threats and not the constant stimulation provided by today's aggressive athletes and fat loss fanatics. Ongoing training results in cortisol levels that do not return to normal for extended periods of time and thereby result in the breakdown or loss of muscle tissue.

After strenuous exercise, muscle tissue enters a stage of rapid nitrogen absorption in the form of amino acids and small peptides in order to rebuild the muscle fibers, grow and add new muscle fibers. During this period of repair and growth, it is important that the muscle cells have available to them sufficient levels of nitrogen in the form of amino acids. While the total level of amino nitrogen is important, the ratios of the various amino acids to each other is even more important.

Athletes and dieters that over-train sometimes enter into a catabolic condition. Muscle catabolism occurs when the athlete or dieter enters a negative nitrogen balance. People on diets usually have a negative nitrogen balance and therefore lose muscle when they lose weight. In contrast, a positive nitrogen balance means the animal has enough nitrogen left over to synthesize muscle proteins.

Various organizations have propounded a list of essential amino acids which are required on a daily basis for proper nutrition. These amino acid requirements vary throughout the growth cycle of all animals. Human muscle tissue is made up of specific amino acids and at specific ratios. If any of these amino acids are missing or deficient, the muscles will not grow, will grow slowly or may even begin to breakdown. However, if the animal is supplied with adequate amounts of protein that contain all of the muscle amino acids, this protein or source of consumed amino nitrogen will be able to support rapid muscle recovery and growth.

The amino acids leucine, isoleucine and valine are the branched chain amino acids and are necessary for a positive nitrogen balance and muscle growth. The branched chain amino acids are lost at significant levels during strenuous exercise and therefore it is critical that they be available during the anabolic state.

The present invention is based in part, upon the discovery that the use of pyruvate in combination with an anabolic protein composition, produces a synergistic effect in increasing the lean body mass or muscle tissue of a mammal consuming same while at the same time decreasing the deposition of fat in the body. The inventive compositions are also effective for increasing the rate of fat loss and decreasing the percent body fat in the mammal and under the proper conditions of caloric intake and exercise results in an overall weight loss in the mammal without significant loss of muscle tissue. The anabolic protein composition itself, when administered in combination with a hypercaloric diet and strenuous exercise, has been found to decrease the percent body fat in a mammal while increasing muscle mass, however, the mammal actually gains weight.

As used herein and the claims, the term "pyruvate" means any salt or ester of pyruvic acid. Pyruvic acid has the formula:

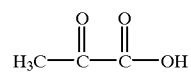

Pyruvic acid is a colorless liquid with an odor resembling that of acetic acid and has a melting point of 13° C. Pyruvic acid is an intermediate in the breakdown of sugars to alcohol by yeast. The mineral salts of pyruvic acid, such as magnesium pyruvate or calcium pyruvate or mixtures thereof are useful in the present invention. Sodium pyruvate is not especially preferred as it is known that sodium is associated with various negative medical conditions such as high blood pressure, water retention and heart disease. Further, certain athletes, such as bodybuilders, desire to present a defined visual image of their body which shows muscle definition and thus, the water retention properties of the sodium salt are not beneficial. Pyruvate precursors in the form of pyruvamides or pyruvyl-amino acids are also useful in the present invention. Pyruvyl-glycine and pyruvyl-glutamine are representative of useful pyruvyl-amino acids. Another pyruvate precursor is pyruvyl-creatine. Pyruvyl-creatine is a covalently linked adduct of pyruvic acid and creatine.

Pyruvate has a number of useful applications in medicine. Pyruvate has been described for retarding fatty deposits in livers (U.S. Pat. No. 4,158,057); for treating diabetes (U.S. Pat. No. 4,874,790); for retarding weight gain (U.S. Pat. Nos. 4,812,879, 4,548,937, and 4,351,835); to increase body protein concentrations in a mammal (U.S. Pat. No. 4,415,576); for treating cardiac patients to increase the cardiac output without accompanying increase in cardiac oxygen demand (U.S. Pat. No. 5,294,641); for extending athletic endurance (U.S. Pat. No. 4,315,835); for retarding cholesterol increase (U.S. Pat. No. 5,134,162); for inhibiting growth and spread of malignancy and retarding DNA breaks; and for inhibiting generation of free radicals. All of these references are incorporated herein by reference.

U.S. Pat. No. 4,981,687 discloses compositions and methods for achieving improved physiological response to exercise. More specifically, this patent teaches a beverage comprising water, sugar, electrolytes, glycerol and pyruvate; and its use to ameliorate the effects of physical exertion. The teachings of U.S. Pat. No. 4,981,687 are incorporated herein by reference.

U.S. Pat. No. 5,719,119 to Veech discloses non-hyperchloremic, alkalinizing aqueous solutions for parenteral nutrition comprising water, numerous amino acids, pyruvate and at least one cation. This patent does not suggest an anabolic protein composition which is designed to mimic the amino acid profile of human muscle tissue.

U.S. Pat. No. 5,089,477 discloses the use of pyruvate in a liquid composition that is used to prevent weight loss in agricultural animals resulting from dehydration.

U.S. Pat. Nos. 5,147,650 and 5,238,684 disclose and claim a fluid composition comprising water, electrolytes, sugar, glycerol, lactate and pyruvate. The teachings of U.S. Pat. Nos. 5,147,650 and 5,238,684 are incorporated herein by reference.

U.S. Pat. No. 5,236,712 discloses and claims a beverage containing water, electrolytes, pyruvate and alanine in a concentration of from about 0.5% to about 10%. The teachings of U.S. Pat. No. 5,236,712 are incorporated herein by reference.

Pyruvate in various forms has been proposed for enteral administration and for parenteral administration. Typically, pyruvates are available in the form of salts, for example, calcium pyruvate and sodium pyruvate. U.S. Pat. Nos. 5,283,260 and 5,256,697 disclose uses for the pyruvyl-amino acids and methods for their production. Pyruvate is also presently available in the form of pyruvyl-creatine adducts. It is believed that this compound, when ingested, dissociates into the ionic forms of pyruvate and creatine.

Pyruvate has been administered to mammals enterally or parenterally typically at superphysiological levels. The amount of pyruvate administered generally ranges from 1 to 20% of the mammal's caloric intake. For enteral dosage, the pyruvate may be disbursed or dissolved in a beverage product or may be included in cookies, candies or other foods. Pyruvate may also be introduced as an aqueous solution parenterally.

The amino acid composition of numerous proteins, biologically active polypeptides and foods, has been known for some time. One pre-eminent monograph on this subject is the Amino Acid Handbook by Richard J. Block, C. C. Thomas, publisher, 1956 (Library of Congress Catalog Card No. 56-9104). On page 343 at Table V, the approximate average amino acid composition of all mammalian muscle proteins, is set forth as follows:

| Amino Acid | Grams/100 gm of Protein |
| --- | --- |
| Arginine | 6.6 |
| Histidine | 2.8 |
| Lysine | 8.5 |
| Tyrosine | 3.1 |
| Tryptophan | 1.1 |
| Phenylalanine | 4.5 |
| Cystine | 1.4 |
| Methionine | 2.5 |
| Serine | 5.1 |
| Threonine | 4.6 |
| Leucine | 8.0 |
| Isoleucine | 4.7 |
| Valine | 5.5 |
| Glutamic Acid | 14.6 |
| Aspartic Acid | 8.0 |
| Glycine | 5.0 |
| Alanine | 6.5 |
| Proline | 5.0 |
| Hydroxyproline | 4.7 |

On pages 272–273, of the Amino Acid Handbook the amino acid profile of human muscle tissue is set forth.

Protein supplementation for serious athletes, such as body builders, is well accepted. Typically recommended dosages range between 1.0 and 3.5 gms of quality protein per kilogram of body weight per day. Numerous sources for the protein supplements are known, such as milk, egg, soy, beef and vegetable protein. Isolated fractions of these sources are also known such as ion-exchange whey protein, caseinates, whey protein concentrates, immunoglobulin and egg albumin. Protein supplements typically are provided as powders or tablets. It is also known to provide protein supplementation in the form of peptides (hydrolyzed protein) or even free amino acids. These approaches have two major limitations; cost and taste. While the use of pyruvate is known for various medical indications and the use of protein supplements are known to increase muscle mass, the prior art has failed to recognize or even consider the combination of pyruvate with an anabolic protein composition.

The anabolic protein composition of the present invention is prepared through the combination of various proteins, peptides or amino acid sources to arrive at an amino acid profile that parallels the amino acid profile of human muscle tissue. Consumption of the anabolic protein composition alone will result in an increase in muscle mass, increased rate of fat loss, less catabolism of muscle tissue after strenuous exercise or as a result of disease, weight loss when caloric intake and exercise are properly combined and quicker muscle cell restoration after strenuous exercise. Even more surprising are the synergistic results that can be achieved when pyruvate is combined with the anabolic protein composition of this invention. An additional aspect of the present invention is that the anabolic protein composition alone or in combination with pyruvate can lessen the catabolic effects of diseases such as cancer and AIDS. The prior art has not disclosed or suggested the compositions and methods of the present invention.

DISCLOSURE OF THE INVENTION

There is disclosed an enteral composition comprising pyruvate and an anabolic protein composition. There is further disclosed an anabolic protein composition having an amino acid profile comprising: glutamic acid at about 12–17 weight %; lysine and leucine, each at about 7–11 weight %; valine, aspartic acid, alanine, threonine, serine, proline and phenylalanine, each at about 5–10 weight %; arginine, isoleucine and glycine, each at about 2–6 weight %; and tyrosine, histidine, tryptophan, cystine and methionine, each at about 0.5–5 weight %, based on the total amino nitrogen.

There is further disclosed an anabolic protein composition comprising:

a) albumin protein at about 60–65% by weight;

b) phenylalanine, methionine and valine, each at about 0.3 to 1.5% by weight;

c) isoleucine and alanine, each at about 0.5 to 1.7% by weight;

d) methionine and glutamic acid, each at about 1.0 to 2.2% by weight; and e) proline at about 2.5 to 4.0% by weight. Components b) through e) are preferably added to the albumin protein as free amino acids. In the alternative selected hydrolysate factions may be used in place of the free amino acids.

There is also disclosed an anabolic protein composition comprising:

a) albumin protein at about 15–30% by weight;

b) whey protein isolate at about 60 to 70% by weight;

c) arginine at about 0.1–0.25% by weight;

d) histidine at about 0.05–0.2% by weight;

e) methionine, serine and glycine, each at about 0.1–0.5% by weight;

f) alanine at about 0.6–1.0% by weight; and g) proline at about 0.5–2.0% by weight.

In this embodiment the free amino acids (c–g) are added to the albumin protein and whey protein mixture. In an alternative embodiment selected fractions of a protein hydrolysate with the proper amino acid content may be added to the albumin protein and whey protein.

In one embodiment of the invention the anabolic protein compositions are utilized in methods to increase fat loss, decrease the percent body fat in a mammal, and increase the muscle mass of the mammal. In hypercaloric feeding of the mammal in association with strenuous exercise, whether it be anaerobic or aerobic, the administration of the anabolic protein composition according to the invention results in an overall weight gain in the mammal, however, the percent body fat is decreased while the muscle mass increases.

In a more preferred embodiment of the present invention, the anabolic protein composition comprises the following amino acids in the ranges recited based on 100 gm of protein as set forth in Table I:

TABLE I

| Amino Acid | Range in g/100 gm of Protein |
| --- | --- |
| Arginine | 2.7–5.5 |
| Histidine | 2.0–3.9 |
| Lysine | 7.0–10.1 |

TABLE I-continued

| Amino Acid | Range in g/100 gm of Protein |
| --- | --- |
| Tyrosine | 1.9–4.5 |
| Tryptophan | 1.0–2.7 |
| Phenylalanine | 5.0–8.0 |
| Cystine | 2.0–4.8 |
| Methionine | 1.8–2.5 |
| Serine | 5.0–8.5 |
| Threonine | 5.0–8.3 |
| Leucine | 9.0–11.0 |
| Isoleucine | 3.2–5.0 |
| Valine | 6.0–8.0 |
| Glutamic Acid | 12.0–17.0 |
| Aspartic Acid | 5.0–9.5 |
| Glycine | 2.2–4.5 |
| Alanine | 5.0–7.1 |
| Proline | 6.0–15.0 |

There is yet further disclosed an anabolic protein composition comprising:

a) about 56–60 wt. % whey protein concentrate;

b) about 9.5–13.5 wt. % albumin protein;

c) about 0.5–2.5 wt. % phenylalanine;

d) about 1.6–3.6 wt. % proline; and e) about 0.05–1.5 wt. % of each of histidine, methionine, serine, glycine and alanine.

Those skilled in the art appreciate that the covalent link, so-called sulfur bridges, between the cysteine residues creates the amino acid dimer referred to as cystine (dicysteine). Thus if the anabolic protein is reported in terms of cysteine content the claimed cystine value ranges would be doubled for cysteine. In an embodiment of the anabolic protein composition the value for proline represents the sum of proline and hydroxyproline. The "universal" genetic code, which is nearly identical in all known life forms, specifies the "standard" amino acids of which proline is one. L-proline and L-hydroxyproline are not strictly amino acids but imino being attached by both ends to give the aliplatic cyclic structure. Nevertheless, many other amino acids are components of certain proteins. In all known cases, these unusual amino acids result from the specific modification of an amino acid residue after the polypeptide chain has been synthesized. Thus, proline is hydroxylated in vivo to make hydroxyproline. Enzymes present in the body convert proline to hydroxyproline, after the proline has been incorporated into, for example, collagen. Since collagen is a major component of connective tissues and occurs in virtually every tissue, the anabolic protein composition of the present invention contains 6.0 to 15 gms of proline per 100 gms of protein. Hydroxylysine may also be subject to enzymatic production. Two additional amino acids that are often reported in the literature and not recited herein are asparagine and glutamine. L-asparagine is very widely distributed in plants and probably plays a part in the synthesis of proteins. It is hydrolyzed rapidly to aspartic acid in the presence of acids or alkalis, to aspartic acid. Glutamine is the monoamide of glutamic acid and is also widely distributed in plants. It plays a similar role to that of its homologue asparagine in the nitrogen metabolism of plants. Glutamic acid is one of the acidic amino acids and is present in large quantities among the products of protein hydrolysis.

There is further disclosed a method for increasing the fat loss of a mammal, said process comprising administering to a mammal in need of increased fat loss, a composition comprising an anabolic protein composition with or without pyruvate. The present invention is also concerned with a method to ameliorate the catabolic effects of diseases such as cancer and AIDS. The method comprises the administration of the anabolic protein composition of the present invention with or without pyruvate.

The present invention is also directed to a method of weight loss in a mammal, said method comprising: 1) the administration to a person in need of such weight loss, a composition comprising pyruvate and an anabolic protein composition; and 2) the co-administration to a person in need of weight loss a hypocaloric diet. By hypocaloric diet is meant that the total calories absorbed per day by an individual (from diet and the pyruvate-anabolic protein composition) is less than or equal to the total caloric expenditure of the individual per day.

Another aspect of the invention is directed to a method of decreasing the body fat and increasing the muscle mass of a mammal, the method comprising the administration to the mammal the anabolic protein composition disclosed above. A further aspect of the invention is directed to a method of increasing the weight of a mammal without increasing its percent body fat. The method comprises the administration of the anabolic protein composition in combination with a hypercaloric diet and exercise. The exercise may be aerobic and/or anaerobic. Further, all of these methods can be accomplished through co-administration of the anabolic protein composition and pyruvate.

The weight ratio of pyruvate to anabolic protein composition can range from about 1:1 to about 1:50. More preferably, the weight ratio of pyruvate to anabolic protein composition is 1:5 to 1:20. The amount of the pyruvate and anabolic protein composition administered to the mammal ranges from 1 to 300 gms per day. More preferred, the mammal should consume from 25 to 75 gms per day. On a weight to weight basis, the amount of the anabolic protein/pyruvate composition consumed by the mammal can range from 1.0 to 4.0 gms per kilogram of body weight per day, more preferably 2.0–3.5 gms per kilogram of body weight per day.

Specific forms of pyruvate useful in the present invention include sodium pyruvate, magnesium pyruvate, calcium pyruvate, potassium pyruvate, pyruvyl-glycine, pyruvyl-creatine, pyruvamines, pyruvyl-alanine, pyruvyl-glutamine, pyruvyl-leucine, pyruvyl-valine, pyruvyl-isoleucine, pyruvyl-phenylalanine, pyruvyl-proline, pyruvyl-sarcosine, their amides, esters and salts, and mixtures thereof.

Pyruvyl-creatine is an especially preferred form of pyruvate. Creatine is a compound that is synthesized in the liver to supply energy to muscle tissue. In the muscle cell creatine is converted to phosphocreatine. The average human metabolizes about 2 gms of creatine per day and about that same amount is synthesized per day. Phosphocreatine is stored in the muscle cell until it is used to produce ATP, thereby forming creatinine which is excreted in the urine. About 1–2 gms is excreted daily by an adult man or woman, and the amount is remarkably constant, the actual quantity being roughly proportional to the body muscular tissue. Presently creatine monohydrate supplementation is popular with athletes and certain studies have indicated that it possibly accelerates fat loss.

The composition of the present invention may include other materials such as fats, carbohydrates, vitamins, minerals, sweeteners, flavoring agents and the like. For example, the synergistic composition of the present invention, pyruvate plus anabolic protein composition, may be combined with known food ingredients or dispersed in a liquid such as orange juice, and consumed orally. In similar fashion the anabolic protein compositions of the invention may be combined with additional components, such as fats, flavoring agents, sweeteners and the like. The anabolic protein composition may be consumed in the form of a pill, tablet, liquid or solid food composition.

In the method of the present invention, the mammal, preferably a human, consumes at least 25 gms per day of the pyruvate/anabolic protein composition. On a percent of calories basis, the synergistic combination can comprise from 1 to about 50% of total caloric intake. The anabolic protein composition itself can be consumed at levels of from about 10 to 100 gms or more per day.

In a preferred embodiment, the pyruvate is in the form of pyruvyl-creatine, calcium, potassium or magnesium pyruvate or mixtures thereof and the anabolic protein composition comprises intact protein, optionally hydrolyzate fractions and/or free amino acids, wherein 100 gms of said anabolic protein composition comprises 2.7 to 5.5 gms of arginine, 2.0 to 3.9 gms of histidine, 7.0 to 10.1 gms of lysine, 1.9 to 4.5 gms of tyrosine, 1.0 to 2.7 gms of tryptophan, 5.0 to 8.0 gms of phenylalanine, 2.0 to 4.8 gms of cystine, 1.8 to 2.5 gms of methionine, 5.0 to 8.5 gms of serine, 5.0 to 8.3 gms of threonine, 9.0 to 11.0 gms of leucine, 3.2 to 5.0 gms of isoleucine, 6.0 to 8.0 gms of valine, 12.0 to 17.0 gms of glutamic acid, 5.0 to 9.5 gms of aspartic acid, 2.2 to 4.5 gms of glycine, 5.0 to 7.1 gms of alanine, and 6.0 to 15 gms of proline.

As used herein and in the claims, the term "amino nitrogen source", "source of amino nitrogen" or "anabolic protein composition" is meant to mean intact protein such as sodium caseinates, whey protein, soy protein, hydrolyzed proteins, fractions of hydrolyzed proteins, meat proteins, vegetable proteins, peptides, free amino acids and mixtures thereof. The anabolic protein composition useful in this invention can be a blend of numerous sources of amino nitrogen or of just a few. The required aspect of this invention is that the amino acid profile of the anabolic protein composition resemble the amino acid profile of human skeletal muscle tissue.

A further aspect of the present invention relates to a method to arrive at an amino acid profile for an anabolic protein composition that is similar to human skeletal muscle tissue. The method comprises the steps of: a) setting a target human muscle tissue amino acid profile, for example, as set forth in Table 1, (hereinafter referred to as Target); b) selecting a predominant source of amino nitrogen for the anabolic protein composition (hereinafter referred to as Protein Source 1); c) obtaining amino acid profiles (typically on a 100 gm protein basis) for Protein Source 1; d) comparing the amino acid profiles of Target with Protein Source 1 to determine those amino acids in Protein Source 1 that exceed the maximum allowable levels in Target; e) calculate maximum amount of Protein Source 1 that may be used to formulate Target by dividing gms of selected amino acid of Protein Source 1 by gms of Target amino acid to yield a value aK that will be less than 1.0; f) repeat step e) for each amino acid; g) select the lowest aK from steps e) and f) and designate aK1; h) determine the amount of Protein Source 1 to be used to prepare 100 gms of Target by multiplying aK1 by 100; i) obtaining free amino acids; and j) adding free amino acids to Protein Source 1 to achieve Target amino acid profile.

The method according to the invention can also be used with two Protein Sources. For example, when an individual amino acid addition is required and that amino acid is either unavailable or undesirable in some way, a second Protein Source (Protein Source 2), rich in that particular amino acid can be used to replace part of the Protein Source 1 using the same method of calculating levels as set forth above.

The present invention also contemplates the separate oral administration of the pyruvate and the anabolic protein composition. Therefore, dosages of each component can occur separately, provided both components are found systematically in the mammal prior to, during and/or subsequent to strenuous exercise. The present invention also contemplates the use of genetically engineered plants, animals and/or organisms to produce the anabolic protein composition.

The inventive pyruvate/anabolic protein composition of this invention is also useful to increase the energy levels and general well being of a mammal. The inventive composition can be used as a food additive, i.e., added to pancake mix or consumed in the form of pills, candies, confections, capsules or powders.

In order to demonstrate the present invention, the following examples are submitted.

EXAMPLE I

Preparation of the Anabolic Protein Composition

One aspect of the present invention resides in the novel anabolic protein composition. This protein composition, which is based upon the amino acid profile of human muscle, provides the catabolic human (from strenuous exercise, diet or disease) with the proper balance of amino acids to prevent degradation of lean body mass or to increase body protein concentration.

Those skilled in the arts of nutrition, protein chemistry and food science will appreciate that numerous sources of amino nitrogen can be blended to arrive at the claimed amino acid profile. Also contemplated within the scope of the present invention is the production of the anabolic protein composition through the use of recombinant or transgenic technologies. For example, a bacteria such as *E. Coli* can be provided with a gene that encodes the production of the anabolic protein composition or a lactating mammal may have a gene inserted into its genome that produces the anabolic protein composition. The anabolic protein would then be isolated from the milk and used in accordance with the present invention.

A representative anabolic protein composition according to the present invention was prepared by blending the following components at the recited percent by weight. The values have been corrected for actual percent of each raw material as to source of amino nitrogen.

| Ingredient | % by Weight |
| --- | --- |
| Whey Protein Concentrate | 26.64 |
| Calcium Sodium Caseinate | 20.29 |
| High Protein Rice Flour | 21.01 |
| Meat Protein Concentrate | 15.02 |
| Egg White Solids | 13.00 |
| L-Leucine | 0.36 |
| L-Lysine | 2.17 |
| L-Arginine | 0.14 |
| L-glycine | 1.37 |

This representative anabolic protein composition was a blend of the following commercially available materials:

1) Whey Protein Concentrate: CALPRO 75 A product of New Zealand Milk Products, Inc. of Petaluna, Calif.;
2) Calcium Sodium Caseinate: Alanate 220 A product of New Zealand Milk Products, Inc. of Petaluna, Calif.;
3) High Protein Rice Flour A product of California Natural Products of Manteca, Calif.;
4) Meat Protein Concentrate: AMPRO 600 A product of American Meat Protein Association of Ames, Iowa;
5) Egg White Solids: Type PF-1 A product of Henningsen Foods, Inc. of Omaha, Nebr; and
6) Amino acids which are obtainable from various sources.

This blend of raw materials resulted in an amino acid profile approximately as follows:

| Amino Acid | % by Wt. |
| --- | --- |
| Glutamic Acid | 16.6 |
| Leucine | 9.5 |
| Lysine | 7.0 |
| Valine | 6.0 |
| Arginine | 4.8 |
| Isoleucine | 5.0 |
| Aspartic Acid | 9.3 |
| Alanine | 5.7 |
| Threonine | 5.1 |
| Glycine | 3.1 |
| Serine | 5.5 |
| Proline | 6.8 |
| Phenylalanine | 5.0 |
| Tyrosine | 4.0 |
| Histidine | 2.8 |
| Tryptophan | 1.3 |
| Cystine | 1.9 |
| Methionine | 2.3 |

The raw materials were blended using standard techniques known in the industry. Calcium pyruvate was added to the anabolic protein to produce the inventive mixture used in Example II.

EXAMPLE II

Three groups of 10 rats each (Control, Control Pyruvate and Control Anabolic Protein Composition), each weighing about 200 gms, is fed a standard laboratory diet supplemented as described below, for a period of 60 days. The standard rat diet contains 15% protein, 28% fat and 57% carbohydrate. A fourth group of 10 rats (Experimental) is fed the same standard diet as the Controls, except for the addition of a mixture of calcium pyruvate and the anabolic protein composition. The anabolic protein composition is set forth in Example I. The mixture is 15% by wt. calcium pyruvate and 85% by wt. anabolic protein composition. The weight ratio of pyruvate to anabolic protein composition is thus 1:5.7. The Experimental group diet is a 90 wt. % blend of the standard diet with 10 wt. % of the inventive mixture. The Control diet is iso-energetically supplemented with maltose-dextrine and the electrolyte composition of the Control diet is made equal to the Experimental diet by adding appropriate amounts of calcium carbonate and sodium citrate. The Control Pyruvate diet contains the same amount of pyruvate as the Experimental and is iso-energetically supplemented with ion exchange whey protein to account for the missing anabolic protein composition. The Control Anabolic Protein Composition diet contains the same level of anabolic protein composition as the experimental and is iso-energetically supplemented with maltose-dextrine, calcium carbonate and sodium citrate to account for the missing pyruvate. Over the 60 day feeding period, the chow and water were provided ad libitum.

Data on diet consumption per day is collected and the animals are also weighed daily. On days 7, 21, 39 and 60 post feeding, the rats are evaluated for total body fat using the water tank method known to those skilled in the art. On day 7 post feeding, each rat is placed in an exercise cage driven by an electric motor. The speed of the exercise cage is set at 100 rpm. The time for each rat to fail to keep up with the set speed is measured. Failure to meet the set speed of the wheel is determined when the rat becomes inverted within the cage. The time to failure is a measure of endurance of the rat. This procedure of exercise to exhaustion is performed daily except for days 14, 21, 28, 35, 29, 46, 53 and 60.

The exercise cage data will indicate that the average time to exhaustion of the Experimental group is 30% greater than the Control and Control Anabolic Protein Composition groups. The Control Pyruvate rats will demonstrate an approximately 15% longer time to exhaustion than the Control and Control Anabolic Protein Composition rats. This is evidence that the inventive, synergistic composition increases endurance and/or performance in a mammal.

The total body fat data will indicate that the Experimental group has a 15% increase in lean body tissue (muscle) over all the Controls. The data will also indicate that the Experimental group gained 20% less fat than the Control and Control Anabolic Protein Composition groups.

There will be found a marked increase of protein concentration (muscle tissue) in the animals fed the composition of the present invention. The synergistic effect of the present invention provides for an increase in body protein concentration by providing the necessary amino acids for the regeneration and addition of muscle tissue while decreasing the deposition of body fat.

An additional important indicator of the novel synergistic composition's effectiveness has been a significant lowering of the perceived difficulty of long term exercise among individuals that consume the pyruvate/anabolic protein composition. The lower difficulty perceived by individuals receiving the pyruvate/anabolic protein composition of the invention will lead to enhanced physical performance, especially when long term exercise, such as marathons, are involved.

EXAMPLE III

This experiment was conducted to demonstrate that an anabolic protein formula according to the invention can be produced from blending commercially available whey protein, meat protein and free amino acids. The whey protein concentrate was from MD Food Ingredients of Union, N.J. designated Lacprodan D1-9224. This whey protein isolate is a spray dried powder containing high quality whey protein derived from sweet dairy whey. It has a high heat stability, is clear in solution and has a typical analysis as found in Table II.

TABLE II

Analysis of Whey Protein Isolate

| Component | Amount % By Weight |
|---|---|
| Protein (N × 6.38) | 88 (min) |
| Moisture | 6.0 (max) |
| Ash | 4.0 (max) |
| Fat | 0.2 (max) |
| Lactose | 0.2 (max) |

The reported amino acid profile of this whey protein isolate from the manufacturer is found in Table III.

TABLE III

Approximate Amino Acid Profile of Whey Protein Isolate

| Amino Acid | % By Weight of Total N Content |
|---|---|
| Alanine | 4.7 |
| Arginine | 1.9 |
| Aspartic Acid | 11.0 |
| Cysteine * | 1.2 |
| Glutamic Acid | 16.7 |
| Glycine | 1.7 |
| Histidine | 1.9 |
| Isoleucine | 6.1 |
| Leucine | 10.2 |
| Lysine | 9.2 |
| Methionine | 1.8 |
| Phenylalanine | 3.0 |
| Proline | 5.8 |
| Serine | 5.0 |
| Threonine | 7.3 |
| Tryptophan | 1.7 |
| Tyrosine | 3.7 |
| Valine | 5.9 |

* Cysteine was actually reported at 2.4%

The meat protein was Ampro 600 from American Meat Protein Corporation of Ames, Iowa. Ampro 600 is primarily an albumin protein derived from hydrolyzed meat that is low in flavor and 100% water soluble. A typical analysis of Ampro 600 is set forth in Table IV.

TABLE IV

Analysis of Ampro 600

| Component | % By Weight |
|---|---|
| Protein | 70.00 |
| Fat | 2.50 |
| Moisture | 6.00 |
| Ash | 11.00 |
| Carbohydrate | 5.00 |
| pH | 8.5 |

The amino acid profile of Ampro 600 is set forth in Table V.

TABLE V

Amino Acid Profile of Ampro 600

| Amino Acid | mg/gm Of Protein |
|---|---|
| Cystine | 22.40 |
| Valine | 43.80 |
| Methionine | 7.20 |
| Isoleucine | 16.30 |
| Leucine | 56.80 |
| Tyrosine | 31.10 |
| Phenylalanine | 33.60 |
| Hydroxylysine | 0.10 |
| Histidine | 24.80 |
| Arginine | 47.80 |
| Tryptophane | 12.90 |
| Aspartic Acid | 68.00 |
| Threonine | 47.40 |
| Serine | 45.60 |
| Hydroxyproline | 13.30 |
| Gluramic Acid | 88.00 |
| Proline | 32.10 |
| Glycine | 24.40 |
| Alanine | 31.20 |
| Lysine | 61.30 |

The Ampro 600 (albumin protein) was dry blended with maltodextrin, the whey protein isolate and the following amino acids as set forth in Table VI. Using the procedure described above it was determined that based on the amino acid profiles of the AMP 600 and the Lacprodan whey protein isolate (WPI) that AMP600 should comprise 23.37% by weight and the WPI should comprise 65.05% by weight of the total composition, the balance comprising the free amino acid and the maltodextrin.

TABLE VI

Dry Blending of Protein Sources and Amino Acids

| Component | % By Weight |
|---|---|
| Ampro 600 (70% protein) | 23.37 |
| Whey Protein Isolate (88% protein) | 65.05 |
| Arginine | 0.17 |
| Histidine | 0.09 |
| Phenylalanine | 1.79 |
| Methionine | 0.34 |
| Serine | 0.34 |
| Leucine | 0.51 |
| Valine | 0.77 |
| Cystine | 0.5 |
| Glycine | 0.34 |
| Alanine | 0.85 |
| Proline | 1.0 |
| Maltodextrin | 5.04 |

Maltrodextnrn was added as filler for purposes of achieving 100% of the recited amino acids in 100 gms of finished product. The amino acid profile for this anabolic protein composition is set forth in Table VII.

TABLE VII

Amino Acid Profile
Grams of Amino Acid per 100 gms of Protein

| Amino Acid | Grams |
|---|---|
| Arginine | 2.79 |
| Histidine | 2.06 |
| Lysine | 7.86 |
| Tyrosine | 3.34 |
| Tryptophan | 1.49 |
| Phenylalanine | 5.04 |
| Cystine | 2.22 |
| Methionine | 1.81 |
| Serine | 5.01 |
| Threonine | 6.21 |
| Leucine | 9.01 |
| Isoleveine | 4.55 |
| Valine | 6.06 |
| Glutamic Acid | 13.63 |
| Aspartic Acid | 9.25 |
| Glycine | 2.23 |
| Alanine | 5.02 |
| Proline + | 6.15 |

The dry blend prepared in accordance with Table VI was then combined with additional ingredients to prepare a nutritional product that readily dissolves in water or milk and has a pleasant flavor and aroma. The formula to prepare a vanilla flavored human muscle protein product is set forth in Table VIII.

TABLE VIII

Vanilla Flavored Anabolic Protein Composition

| Ingredient | Amount in Pounds |
|---|---|
| Maltodextrin | 30.46380 |
| Canola Oil | 1.25000 |
| Natural Flavor Blend | 0.50000 |
| Anabolic Protein from Table VI | 60.500 |

TABLE VIII-continued

Vanilla Flavored Anabolic Protein Composition

| Ingredient | Amount in Pounds |
|---|---|
| Mineral Premix | 0.03510 |
| Beta Carotene 1% CWS | 0.10000 |
| Vitamin Premix | 0.35640 |
| Choline Bitartrate | 0.27010 |
| Magnesium Oxide USP | 0.45000 |
| Tricalcium Phosphate | 0.80000 |
| Potassium Chloride USP | 0.14960 |
| Vanilla Flavor | 1.00000 |
| Aspartame | 0.20000 |
| Acesulfame-K | 0.10000 |
| Carrageenan | 0.25000 |
| Xanthan Gum | 0.25000 |
| CMC Gum | 0.82500 |
| Guar Gum | 2.50000 |

All components were dry blended and then packaged into 2 pound containers.

EXAMPLE IV

In a manner similar to Example 3 an anabolic protein composition was prepared except that only one primary source of intact protein was used. Table IX sets forth the formula.

TABLE IX

| Component | % By Weight |
|---|---|
| AMP 600 (70% protein) | 88.99 |
| Phenylalanine | .86 |
| Methionine | .74 |
| Leucine | 1.88 |
| Isoleucine | 1.02 |
| Valine | .73 |
| Glutamic Acid | 1.43 |
| Alanine | 1.08 |
| Proline | 3.27 |

The resulting composition resulted in an approximate amino acid profile set forth in Table X.

TABLE X

Amino Acid Profile
Grams of Amino Acid per 100 gms of Protein

| Amino Acid | Grams |
|---|---|
| Arginine | 5.50 |
| Histidine | 2.85 |
| Lysine | 7.07 |
| Tyrosine | 3.58 |
| Tryptophan | 1.49 |
| Phenylalanine | 5.00 |
| Cystine | 2.58 |
| Methionine | 1.80 |
| Serine | 5.25 |
| Threonine | 5.45 |
| Leucine | 9.00 |
| Isoleueine | 3.20 |
| Valine | 6.00 |
| Glutamic Acid | 12.00 |
| Aspartic Acid | 7.82 |
| Glycine | 2.81 |
| Alanine | 5.00 |
| Proline | 9.50 |

EXAMPLE V

Clinical Evaluation

This experiment is designed to demonstrate the effectiveness of the anabolic protein composition according to the invention. The protein composition as prepared in Table VIII is fed to subjects with and without pyruvate to evaluate weight loss, changes in body composition, changes in mood states, and plasma lipid levels.

A double blind, placebo controlled protocol is developed wherein twenty (20) subjects with a mass index (BMI) of greater than twenty five (>25) were divided into three groups. Group A receives 6 gms of calcium pyruvate and 60 gms of the anabolic protein composition set forth in Table VIII daily. Group B receives a maltodextrine placebo while Group C receives 60 gms of the anabolic protein composition daily for the six week study. The subjects are instructed by a registered dietitian to follow an American Heart Association Step One Diet and a three day per week circuit exercise program which is supervised by an exercise physiologist.

Subjects are excluded from the study if they are currently following a reduced calorie diet, are taking anorectic medications (i.e. phentermine, silbutramine, etc.), have a history of thyroid disease, HIV/AIDS, cancer or any wasting syndrome. Subjects are also excluded if they had never exercised before. Capsules for the calcium pyruvate or the maltodextrine placebo (Group A and Group B) are the same in terms of size, shape, color and weight. Each group is instructed to take six capsules per day, two with each main meal. The 60 gms of anabolic protein composition is added to water and stirred. Subjects are instructed to divide the 60 gm daily dose into 2 or 3 administrations per day.

Each subject is evaluated at baseline, week three, week six, and conclusion. Total body weight is measured using a Detecto™ balanced medical scale at each laboratory visit. Subjects are weighed after a four hour fast and voiding of the bladder. After four hours of fasting, body composition is measured via bioelectric impedance analysis (Biodynamics 3.10, Seattle, Wash.). All participants refrain from caffeine the day prior to body composition analysis and subjects are prohibited from drinking alcohol throughout the study.

All subjects engage in a three day a week circuit training exercise program under the guidance of an exercise physiologist. The exercise sessions last for about forty five (45) minutes. The exercise program consists of a combination of step aerobics and weight training. The subjects are requested to stay on the 1800 calorie American Heart Association Step One Diet and are given meal plans, daily menus and restaurant guidelines. Each subject is also followed up by telephone from a registered dietitian and multiple twenty-four (24) hour dietary recalls are also taken at baseline, week three and week six.

Perceived Energy

The subjects of the study are also evaluated to determine if the inventive weight control product had any impact on the subjects feelings of vigor or fatigue. A Profile of Mood States questionnaire (POMS) is employed to determine if the supplementation had any impact on these feelings. The questionnaire is from the Educational and Industrial Testing Service of San Diego, Calif. The POMS questionnaire has previously been validated as a method to determine significant differences in subjective feelings while participating in a study. Each study subject takes the POMS at each laboratory visit.

Biochemical Parameters

Serum chemistries, complete blood count, total cholesterol and triglycerides are assessed at baseline, week 3, and week 6 during scheduled laboratory visits. The blood is drawn via the antecubital vein. Urinalysis is also conducted at each laboratory visit and tested for any effect on urinary glucose or protein. Specific gravities are also measured as an indication of dehydration.

Statistical analysis is conducted for each group and is tested for intergroup and intragroup variance. Fisher's exact test is utilized for baseline characteristics of the three groups while a Kruskal-Wallis Test is employed to test the continuous variables. Significance is set up a p value of <0.05.

Results

The results will demonstrate that Group A will lose a significant amount of body weight and body fat as compared to Group B (control) and slightly more than Group C. Group A will also demonstrate a significant reduction in their fatigue as compared to other groups, that is, they feel less tired over time with the supplement according to the present invention. Group A will also experience a significant increase in vigor as they feel more energetic over time with the pyruvate/anabolic protein supplement. A significant decrease in body fat with associated percent increase in muscle mass will also be seen in Groups A and C. All three groups will lose a percentage of body fat however, Groups A and C will lose significantly more body fat than the placebo group. In terms of actual fat weight loss, Group A will lose more than Group C, however, Groups A and C will lose significantly more than Group B (control). From another prospective, Groups A and C will lose more fat than the control group. An analysis of the blood chemistries will also demonstrate that Groups A and C experienced a trend towards better blood sugar values and a decrease in blood serum lipid levels.

In one preferred embodiment of the present invention, there is provided a container or package containing a pharmaceutically acceptable mixture of pyruvate and anabolic protein composition in a unit dosage quantity (i.e., pills or capsules) together with instructions for administration of effective quantities over a period of time. In another embodiment, the synergistic composition of this invention is in combination with a liquid or powdered base, such as glucose, flavoring agents or carbohydrates to improve patient acceptance of the composition. The composition of this invention or the available protein composition alone may also be incorporated as an ingredient in a foodstuff such as cookies, pretzels, candies, chewing gums, rehydration solutions and the like.

Industrial Applicability

The weight control product of the invention provides an unexpected benefit in weight loss, fat loss, mood elevation and the lowering of blood plasma lipid levels. The medical community and consumers at large will readily accept the inventive product as it provides outstanding results and is economically produced, with no known side effects.

The medical community and the serious athlete are constantly searching for compositions and methods that will enhance athletic performance and/or endurance while also increasing the lean body mass, protein concentration and muscle mass of the athlete. There is also a need for nutritional compositions that will assist the catabolic patient in maintaining weight or preventing further weight loss. Thus, the inventive anabolic protein composition of the present invention either alone or in combination with pyruvate will be useful for patients suffering from cancer or AIDS. There is also a need for compositions which reduce the deposition of body fat and reduce the catabolic effects of strenuous exercise. The present invention is based in part on the synergistic combination of a known chemical entity (pyruvate) and an. anabolic protein composition which surprisingly produces outstanding increases in athletic endurance and performance while also increasing body protein concentration and muscle mass while lessening the deposition of fat in the body. A surprising aspect of the invention is that the anabolic protein composition alone, when combined with an exercise program and reduced calorie intake, will result in an overall weight loss without significant loss of muscle tissue. The present invention will be of substantial benefit to all athletes, especially body builders, weight lifters, dieters and the like.

Although the invention has been described in connection with certain specific embodiments, it will be readily apparent to those skilled in the art that various changes can be made to suit specific requirements without departing from the spirit of and scope of the invention.

What is claimed is:

1. An anabolic protein composition comprising:
   a) albumin protein at about 60–65% by weight;
   b) phenylalanine, methionine and valine, each at about 0.3 to 1.5% by weight;
   c) isoleucine and alanine, each at about 0.5 to 1.7% by weight;
   d) methionine and glutamic acid each at about 1.0 to 2.2% by weight; and
   e) proline at about 2.5 to 4.0% by weight.

2. An anabolic protein composition comprising:
   a) albumin protein at about 15–30% by weight;
   b) whey protein isolate at about 60 to 70% by weight;
   c) arginine at about 0.1–0.25% by weight;
   d) histidine at about 0.05–0.2% by weight;
   e) methionine, serine and glycine, each at about 0.1–0.5% by weight;
   f) alanine at about 0.6–1.0% by weight; and
   g) proline at about 0.5–2.0% by weight.

3. A method for increasing the protein concentration, lean body mass or muscle mass in a mammal which comprises administering orally to a mammal in need thereof, a therapeutically effective amount of an anabolic protein composition according to claim 2.

4. The method according to claim 3 wherein said composition additionally comprises pyruvate selected from the group consisting of sodium pyruvate, calcium pyruvate, magnesium pyruvate, potassium pyruvate, pyruvyl-creatine, pyruvyl-glycine, pyruvamines, pyruvyl-alanine, pyruvyl-glutamine, pyruvyl-leucine, pyruvyl-valine, pyruvyl-isoleucine, pyruvyl-phenylalanine, pyruvyl-proline, pyruvyl-sarcosine, their amides, esters and salts and mixtures thereof.

5. The method according to claim 3 wherein said anabolic protein composition comprises glutamic acid at about 12 to 17 weight %; lysine and leucine each at about 7 to 11 weight %; valine, aspartic acid, alanine, threonine, serine, proline and phenylalanine each at about 5 to 10 weight %; arginine, isoleucine and glycine each at about 2 to 6 weight %; and tyrosine, histidine, tryptophan, cystine and methionine each at about 0.5 to 5 weight %.

6. An anabolic protein composition comprising:
   a) about 56–60 wt. % whey protein concentrate;
   b) about 9.5–13.5 wt. % albumin protein;
   c) about 0.5–2.5 wt % phenylalanine;
   d) about 1.6–3.6 wt % proline; and
   e) about 0.05–1.5 wt % of each of histidine, methionine, serine, glycine and alanine.

7. A method for the treatment of catabolism in a human caused by AIDS or cancer, said method comprising the administration of the anabolic protein composition according to claim 6.

8. A method for the treatment of catabolism in a human caused by AIDS or cancer, said method comprising the administration of the composition according to claim 2.

9. A method for decreasing the percentage body fat in a mammal which comprises administering to said mammal a therapeutically effective amount of an anabolic protein composition according to claim 2.

10. A method for ameliorating the effects of physical exertion, said method comprising the administration to a person in need of such amelioration, a composition according to claim 2.

* * * * *